(12) United States Patent
Runyon et al.

(10) Patent No.: US 11,170,887 B2
(45) Date of Patent: Nov. 9, 2021

(54) BODY WEIGHT MANAGEMENT AND ACTIVITY TRACKING SYSTEM

(71) Applicant: Access Business Group International LLC, Ada, MI (US)

(72) Inventors: Matthew K. Runyon, East Grand Rapids, MI (US); Kerry A. Grann, Lansing, MI (US); Michelle R. Marotske, East Grand Rapids, MI (US); Leanne M. Venable, Zachary, LA (US); Corby K. Martin, Baton Rouge, LA (US)

(73) Assignee: Access Business Group International LLC, Ada, MI (US)

( * ) Notice: Subject to any disclaimer, the term of this patent is extended or adjusted under 35 U.S.C. 154(b) by 571 days.

(21) Appl. No.: 15/946,841

(22) Filed: Apr. 6, 2018

(65) Prior Publication Data

US 2018/0294053 A1    Oct. 11, 2018

Related U.S. Application Data

(60) Provisional application No. 62/483,021, filed on Apr. 7, 2017, provisional application No. 62/607,537, filed on Dec. 19, 2017.

(51) Int. Cl.
*G16H 20/60* (2018.01)
*G06F 3/0481* (2013.01)
(Continued)

(52) U.S. Cl.
CPC ......... *G16H 20/60* (2018.01); *G06F 3/04812* (2013.01); *G06F 3/04817* (2013.01);
(Continued)

(58) Field of Classification Search
CPC ........ G16H 20/60; G16H 40/63; G16H 20/30; G06F 3/04812; G06F 3/04817; G06N 7/00
See application file for complete search history.

(56) References Cited

U.S. PATENT DOCUMENTS 5,673,691 A * 10/1997 Abrams ................ G06F 15/025
600/300
6,663,564 B2    12/2003 Miller-Kovach et al.
(Continued)

FOREIGN PATENT DOCUMENTS

EP        2676605 A1    12/2013
JP      2004227522      8/2004
(Continued)

OTHER PUBLICATIONS

Martin et al. "Smartloss:A Personalized Mobile Health Intervention for Weight Management and Health Promotion" JMIR MHealth and UHealth (Mar. 2016); DOI: 10.2196/mhealth.5027 (Year: 2016).*
(Continued)

*Primary Examiner* — Rehana Perveen
*Assistant Examiner* — Alfred H B Wechselberger
(74) *Attorney, Agent, or Firm* — Warner Norcross + Judd LLP

(57) ABSTRACT

An integrated system for delivering weight loss guidance and activity tracking in a mobile format. The integrated system includes a weight loss program hosted on a mobile device. The weight loss program includes an energy intake prescription to guide a participant toward a target weight according to a weight loss prediction model that is visually depicted in a first application window. The mobile device can be paired with a weight sensor to provide weight updates at regular intervals. The mobile device can also be paired with a caloric expenditure measuring device, for example a step counter, to display activity levels for comparison with
(Continued)

recommended activity goals in a second application window. The weight loss program extends over multiple phases that are structured to help individuals gradually achieve a sustainable weight loss while increasing daily activity levels over the duration of the program.

34 Claims, 14 Drawing Sheets

(51) Int. Cl.
    *G06N 7/00*         (2006.01)
    *G16H 20/30*      (2018.01)
    *G16H 40/63*      (2018.01)

(52) U.S. Cl.
    CPC ............... *G06N 7/00* (2013.01); *G16H 20/30* (2018.01); *G16H 40/63* (2018.01)

(56) References Cited

U.S. PATENT DOCUMENTS

| | | | |
|---|---|---|---|
| 7,523,040 B2 | 4/2009 | Kirchhoff et al. | |
| 7,974,881 B2 | 7/2011 | Culver et al. | |
| 8,265,901 B2 | 9/2012 | Petrucelli | |
| 8,398,546 B2* | 3/2013 | Pacione | A61B 5/02055 600/300 |
| 8,600,928 B2 | 12/2013 | Landers | |
| 8,762,102 B2 | 6/2014 | Yuen et al. | |
| 8,956,290 B2* | 2/2015 | Gilley | G06Q 10/109 600/301 |
| 9,011,153 B2 | 4/2015 | Bennett et al. | |
| 9,173,577 B2 | 11/2015 | Yuen et al. | |
| 9,183,498 B2 | 11/2015 | Landers | |
| 9,207,830 B2* | 12/2015 | Papa | G06F 3/04845 |
| 9,392,941 B2 | 7/2016 | Powch et al. | |
| 9,569,483 B2 | 2/2017 | Hall | |
| 2002/0133378 A1* | 9/2002 | Mault | A61B 5/1118 705/3 |
| 2006/0259323 A1* | 11/2006 | Chan | G16H 20/60 705/2 |
| 2007/0208593 A1* | 9/2007 | Hercules | A63B 24/0006 705/2 |
| 2008/0050740 A1 | 2/2008 | Cassidy | |
| 2011/0106553 A1 | 5/2011 | Sato et al. | |
| 2011/0143322 A1 | 6/2011 | Tsang | |
| 2012/0171646 A1 | 7/2012 | Chen et al. | |
| 2013/0179191 A1* | 7/2013 | Bal | G16H 15/00 705/3 |
| 2013/0198214 A1* | 8/2013 | Hall | G06F 19/3475 707/758 |
| 2014/0088995 A1* | 3/2014 | Damani | G16H 15/00 705/2 |
| 2014/0285491 A1 | 9/2014 | Otsubo et al. | |
| 2015/0093725 A1* | 4/2015 | Baarman | G09B 5/00 434/127 |
| 2015/0161911 A1* | 6/2015 | Muto | G06F 19/3475 434/127 |
| 2015/0220697 A1* | 8/2015 | Hunt | G16H 50/30 705/2 |
| 2016/0063888 A1 | 3/2016 | McCallum et al. | |
| 2016/0196766 A1 | 7/2016 | Lundin | |
| 2017/0323582 A1 | 11/2017 | Nusbaum et al. | |
| 2018/0108272 A1* | 4/2018 | Ahmad | G09B 19/0092 |
| 2018/0226155 A1* | 8/2018 | Mahoney | G16H 50/30 |

FOREIGN PATENT DOCUMENTS

| | | |
|---|---|---|
| JP | 2011123582 | 6/2011 |
| WO | 2015116879 A1 | 8/2015 |
| WO | 2017023555 A1 | 2/2017 |
| WO | 2017165621 A1 | 9/2017 |

OTHER PUBLICATIONS

Pieper et al. "Development of adherence metrics for caloric restriction interventions" Clinical Trials, vol. 8, pp. 155-164 [retrieved on Sep. 20, 2021] (Year: 2011).*
Spencer, Melanie D., et al. "Association between composition of the human gastrointestinal microbiome and development of fatty liver with choline deficiency." Gastroenterology 140.3 (2011): 976-986.
Thomas A. Wadden et al., "Efficacy of Lifestyle Modification for Long-Term Weight Control," Obesity Research, vol. 12, Dec. 2004.
D. M. Thomas et al., "Why do individuals not lose more weight from an exercise intervention at a defined dose? An energy balance analysis," International Association for the Study of Obesity, vol. 13, pp. 835-847, Oct. 2012.
Executive Summary: Guidelines (2013) for the Management of Overweight and Obesity in Adults, Obesity, vol. 22, Suppl. 2, Jul. 2014.
Corby K. Martin et al., "Efficacy of SmartLoss, a Smartphone-Based Weight Loss Intervention: Results from a Randomized Controlled Trial," Obesity, vol. 23, No. 5, May 2015.
Deirdre K. Tobias et al., "Effect of low-fat diet interventions versus other diet interventions on long-term weight change in adults: a systematic review and meta-analysis," Lancet Diabetes Endocrinol, vol. 3, pp. 968-979, 2015.
Diana M. Thomas et al., "A simple model predicting individual weight change in humans," Journal of Biological Dynamics, iFirst, 2011, pp. 1-21.
Corby K. Martin et al., "Smartloss: A Personalized Mobile Health Intervention for Weight Management and Health Promotion," JMIR mHealth uHealth, Jan.-Mar. 2016; 4(1); e18.
International Search Report and Written Opinion for related WO Serial No. PCT/US2018/026379, dated Jun. 19, 2018.

* cited by examiner

|  | AUTO / CONNECTION | MANUAL | MISSED / EDITABLE |
|---|---|---|---|
| ON TRACK | 42 ✓ | ◇✓ | ○ |
| CAUTION | 44 ! | ◇! | ○ |
| OFF TRACK | 46 ⊕ | ◇⊕ | ○ |
| MILESTONES | 48 ★ | ◇★ | ★ ○ |

Fig. 3

BODY WEIGHT MANAGEMENT AND ACTIVITY TRACKING SYSTEM

FIELD OF THE INVENTION

The present invention relates to body weight management and activity tracking, and, more particularly, to an integrated system with a graphical user interface for assisting individuals in achieving sustainable weight loss and healthy lifestyle behaviors.

BACKGROUND OF THE INVENTION

Obesity is known to present significant health risks, including an increased risk of heart disease, high blood pressure, and diabetes. According to the Centers for Disease Control and Prevention, an estimated 70% of the U.S. adult population is overweight or obese. In view of the known health risks and relative prevalence of obesity, diet and exercise programs have drawn increased attention in recent years. For example, several commercially available diet programs focus on adherence to a meal plan as the most critical factor in obtaining a healthy weight. These programs include Atkins®, Ornish™, Weight Watchers®, and Zone Diets®. However, many individuals may have difficulty adhering to the prescribed meal plan. In these situations, individuals often do not understand why they are not obtaining their weight loss goals.

Other programs focus on rapid weight loss or have a heavy reliance on exercise to lose weight. So-called "quick win" weight loss programs may deliver weight loss over the short term, but are often unsustainable, and may result in many individuals regaining the weight they have lost. In addition, research has demonstrated that individuals tend to overestimate the energy expenditure associated with physical activity and tend to reward themselves with food after they exercise. Thomas, D. M. et al, "Why do individuals not lose more weight from an exercise intervention at a defined dose? An Energy Balance Analysis," Obesity Reviews 2012, 13:835-47. As a result, it is often the case that the amount of calories consumed after a workout is greater than the amount of calories expended during the workout.

Recently, the National Heart, Lung, and Blood Institute (a research body within the U.S. Department of Health and Human Services) and stakeholders established guidelines for combatting obesity in adults. These guidelines relate to diet, exercise, and behavior modification. "Expert panel report: guidelines (2013) for the management of overweight and obesity in adults," *Obesity* 2014. In light of at least these guidelines, there remains a need for a system that combines diet, exercise, and behavior modification in a manner that is easy to use and that promotes long term sustainable weight loss. In particular, there remains a continued need for a weight loss program that delivers on some or all of the guidelines above in a system to assist individuals in achieving sustainable weight loss and healthy lifestyle behaviors.

SUMMARY OF THE INVENTION

The present invention according to one embodiment provides an integrated system for delivering weight loss guidance and activity tracking in a mobile format. In this embodiment, the integrated system includes a graphical user interface hosted on one or more computer devices, optionally a mobile device. The graphical user interface guides a participant toward a target weight according to a weight loss prediction model that is visually depicted on the mobile device. The mobile device can be paired with a weight sensor to provide weight updates at regular intervals, optionally daily. The mobile device can also be paired with a caloric expenditure measuring device, for example a step counter, to measure activity levels for comparison with recommended activity goals. The weight loss guidance extends over multiple phases of a weight loss program that are structured to help the participant gradually achieve a sustainable weight loss while increasing daily activity levels over the duration of the program.

In one embodiment, the graphical user interface visually depicts, in a first application window, the weight loss prediction model and multiple weight measurements, where the most recent of the depicted weight measurements include a performance flag. The performance flag is selected from among multiple performance flags based on a measure of conformance with the weight loss prediction model. For example, the weight loss prediction model can include an upper boundary and a lower boundary to define a zone of adherence therebetween. The performance flags can include a first, optionally green, performance flag to indicate a weight measurement is within the zone of adherence. The performance flags can include a second, optionally yellow, performance flag to indicate a weight measurement is (a) within the zone of adherence but is greater than or equal to the immediately preceding depicted weight measurement or (b) above the zone of adherence but represents a measured rate of weight loss that is greater than a threshold rate of weight loss. The performance flags can include a third, optionally red, performance flag to indicate a weight measurement is not within or approaching the zone of adherence. The weight measurements are automatically pushed to the mobile device, optionally daily, but can be entered manually, in which instances the performance flags can include a different shape for example. In addition, the participant has the option of publishing weight loss results to social media directly from the first application window, with control over the extent of the content being shared. For example, the participant has the option of publishing the entire weight loss prediction model, a sub-portion of the weight loss prediction model, or only that day's performance flag.

In one embodiment, the graphical user interface visually depicts, in a second application window, the participant's median daily step count as measured by the caloric expenditure measuring device and that depicts a first step goal based on a first activity assessment. At the conclusion of an initial time period, optionally two weeks, the second application window can replace the first step goal with a second step goal that is based, at least in part, on a measure of conformance of the participant's measured weight relative to the weight loss prediction model. For example, the second step goal can include a first percentage increase of the first step goal in response to each of the performance flags from the initial period being first performance flags. Also by example, the second step goal can include a second percentage increase, less than the first percentage increase, in response to any one of the performance flags from the initial period being second performance flags. Still further by example, the second step goal can remain unchanged from the first step goal in response to any one of the performance flags from the initial period being third performance flags. Thereafter, the second application window can revise the step goal each week based upon the performance flags for the prior week.

In one embodiment, the graphical user interface provides pre-programmed feedback as part of the weight loss program, the pre-programmed feedback being structured to provide behavior modification guidance. In this embodiment, the pre-programmed feedback includes four categories of feedback: SmartTips feedback, SmartLoss™ feedback, Milestones feedback, and Ad hoc feedback. The cadence of the foregoing feedback is variable to ensure the pre-programmed feedback does not become overly predictable. For example, the cadence of the SmartLoss™ feedback is dependent upon the performance flags. This feedback is depicted in the first application window as a user-selectable banner that, when selected, provides the scheduled feedback content. Near the conclusion of the weight loss program, the scheduled feedback content can include guidance regarding optimized nutrition, optimized sports nutrition, or health and beauty related products, along with the option to repeat the weight loss program if desired.

In one embodiment, the graphical user interface provides portion tracking in accordance with an energy intake prescription. In this embodiment, the mobile device includes a further application window having a daily food tracker. The mobile device converts meal data from the daily food tracker into portions for proteins, carbohydrates, and fats. The aggregate portions for each such category of food are displayed by the mobile device in connection with a daily portion allowance. The energy intake prescription remains constant throughout the weight loss program, however the mobile device offers a balanced meal plan, a reduced carbohydrate meal plan, and a reduced fat meal plan for the energy intake prescription.

These and other features and advantages of the present invention will become apparent from the following description of embodiments of the invention in accordance with the accompanying drawings and appended claims.

Before embodiments of the invention are explained in detail, it is to be understood that the invention is not limited to the embodiments set forth in the following description or illustrated in the drawings. The invention may be implemented in various other embodiments and may be practiced or carried out in alternative ways not expressly disclosed herein. The phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. The use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 3 includes a table of performance flags for display by the mobile device in the first application window.

DESCRIPTION OF THE CURRENT EMBODIMENT

The present invention relates to body weight management and activity tracking, and, more particularly, to an integrated system including a weight loss program hosted on one or more computer devices, optionally a mobile device including a graphical user interface, for assisting an individual in achieving sustainable weight loss and healthy lifestyle behaviors. Below is a system overview of one embodiment (Part I), a description of various phases of the weight loss program and related assessments (Part II), a description of weight loss tracking and related performance flags (Part III), a description of the administration of activity goals and activity tracking (Part IV), a description of the various categories of feedback available as part of the weight loss program (Part V), a description of meal tracking aids (Part VI), and a description of sharing options for social media (Part VII).

I. Integrated System Overview

Figure 1:
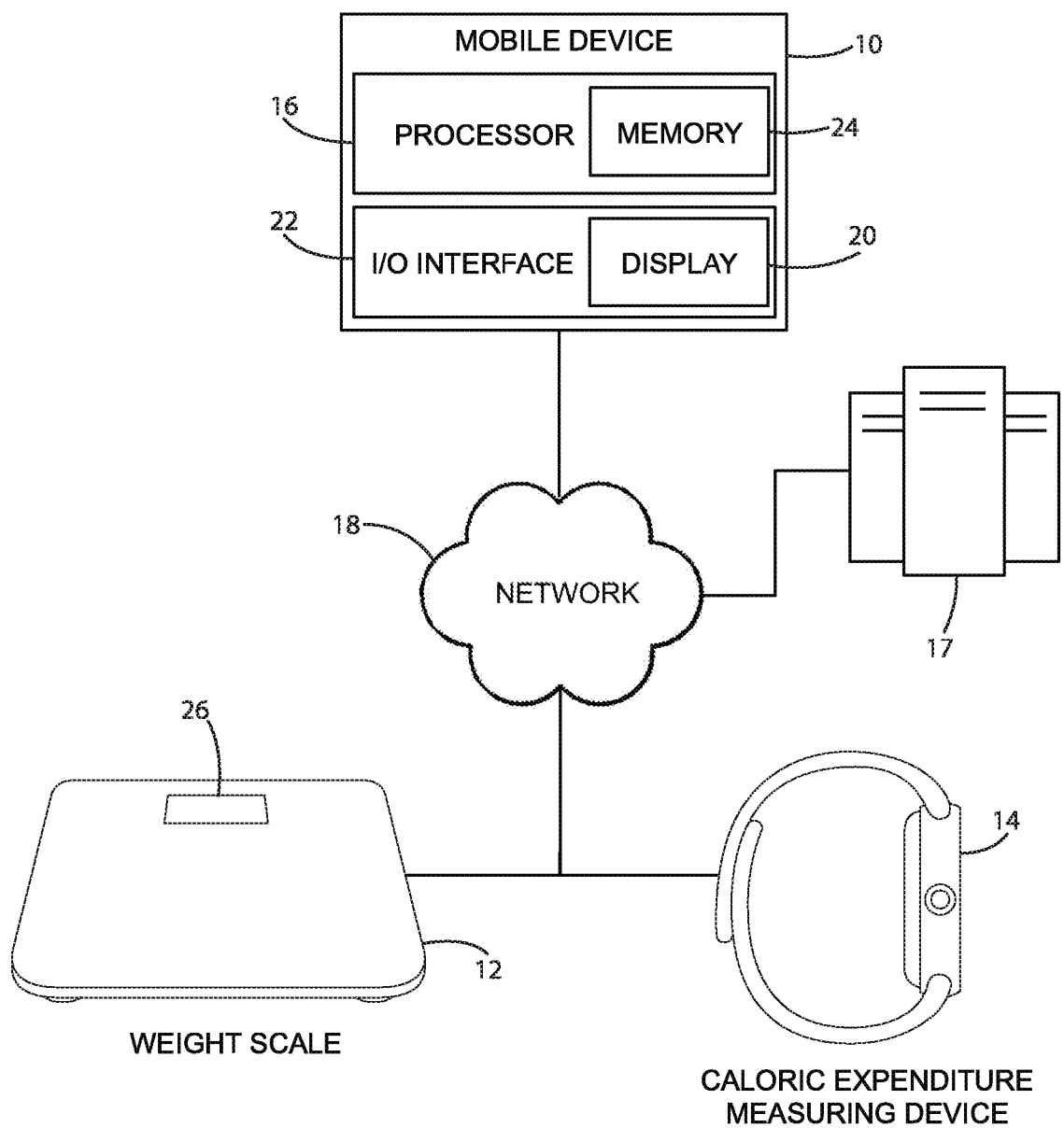
FIG. 1 illustrates an integrated system including a mobile device, a weight scale, and a caloric expenditure measuring device in accordance with one embodiment.

FIG. 1 is a diagram illustrating an integrated system for hosting the weight loss program of the present invention in accordance with one embodiment. According to this embodiment, the system includes a computer device 10, a weight scale 12, a caloric expenditure measuring device 14, and a processor 16 operatively coupled to at least one of the computer device 10, the weight scale 12, and the caloric expenditure measuring device 14. The processor 16 is operatively coupled to, and forms a part of, the computer device 10 in the current embodiment. In other embodiments the processor 16 is operatively coupled to other than the computer device 10. For example, the processor 16 can be remotely hosted on a cloud server or a network of cloud servers 17. Further by example, the processor 16 can be operatively coupled to the weight scale 12 or to the caloric expenditure measuring device 14. Still further by example, the processor 16 can include two or more processors that reside on different devices, e.g., one processor on the mobile device 10 and one processor on a cloud server 17.

As also shown in FIG. 1, the computer device 10, the weight scale 12, the caloric expenditure measuring device 14, and the cloud server 17 are connected over one or more networks 18. The network or networks can include any of the following wireless networks: Bluetooth®, Bluetooth Smart®, ZigBee®, and WiFi™. Still other networks can be used in other embodiments as desired. In still other embodiments, fewer than all four components are connected over a network. For example, in some embodiments the weight scale 12 is a conventional weight scale lacking connectivity. In these embodiments, the weight scale 12 is disconnected from the network 18, and consequently weight data is manually entered as explained more fully in Part III below.

The computer device 10 includes any electronic device adapted to display content to a user. The computer device 10 is optionally a mobile device, for example a smartphone, a tablet, a two-in-one laptop, or a smartwatch. The mobile device 10 includes a display 20, an input/output interface 22, an internal processor 16, and internal memory 24. The input/output interface 22 includes a touch screen graphical user interface in the present embodiment, but can include other interfaces in other embodiments, for example a mouse, a trackpad, and/or a keyboard. The memory 24 includes an instruction set that, when executed by the processor 16, causes the processor 16 to perform certain method steps in the performance of the weight loss program.

The caloric energy measurement device 14 includes any device adapted to measure the activity levels. In the illustrated embodiment, the caloric energy measurement device 14 includes a wearable device, and in particular a wristwatch with an internal step counter. In other embodiments the caloric energy measurement device 14 includes an activity tracker or a pedometer that is attached to an article of clothing, for example a belt, a collar, or a waistband. In still other embodiments the caloric energy measurement device 14 is incorporated into a mobile device 10, in which instance the system does not include a standalone device for measuring activity levels. As shown in FIG. 1, the caloric energy measurement device 14 is connected to a mobile device 10 over the wireless network 18, such that activity levels are communicated to the mobile device 10 in a manner discussed in Part IV below.

Lastly, the weight scale 12 includes any scale adapted to measure a user's body weight. In the illustrated embodiment, the weight scale 12 is a digital scale adapted to measure body weight and sync with the mobile device 10 over the network 18 to allow the mobile device 10 to track body weight over time. In other embodiments, however, the weight scale 12 is a conventional weight scale that does not sync with the mobile device 10 or any other device over a network. In these embodiments, the weight data from a numerical display 26 can be manually entered into the mobile device 10 as more fully set forth in Part III below.

II. Weight Loss Program Overview

The weight loss program is hosted on the mobile device 10, and includes a weight loss component, discussed in Part III below, and an activity tracking component, discussed in Part IV below. Before turning to these components, an overview of the weight loss program according to the current embodiment is presented. The weight loss program according to this embodiment is not limiting, as other embodiments may differ from the current embodiment.

Turning to the current embodiment, the weight loss program includes consecutive phases: a jumpstart phase, a transition phase, a steadfast phase, and a sustain phase. These phases constitute the weight loss program, which concludes after six months unless renewed by the participant in the current embodiment. Each phase is discussed in turn.

The jumpstart phase is the first phase in the weight loss program. The jumpstart phase extends over a first duration, the first duration being four weeks in the current embodiment. The jumpstart phase emphasizes the fundamentals of weight loss and demonstrates that adherence to a calorie-restricted meal plan will likely achieve a predicted weight loss. For example, the jumpstart phase includes a heavy reliance on meal replacement shakes, optionally two meal replacement shakes per day. To determine the calorie restriction, and at the outset of the jumpstart phase, the participant enters an age, gender, height, current weight, and target weight using the graphical user interface 22 of the mobile device 10. In the current embodiment, the participant is restricted from selecting an unsafe target weight. For example, a slider bar depicted on the touch screen display 20 includes the current weight and one end thereof and a minimum safe target weight (e.g., 87.5% of the current weight) at the other end thereof. In response to manipulation of the slider bar, the processor 16 causes the display 20 to depict the approximate change in the overall daily food allowance. As the target weight is lowered (not less than the minimum safe target weight), the overall daily food allowance decreases. As the target weight is raised (not greater than the current weight), the overall daily food allowance increases. By manipulating the slider bar, the participant is shown multiple options, e.g., small, medium, and large, from which to choose by selecting the appropriate target weight.

Based on the foregoing data from the participant, optionally to the exclusion of all other data, the cloud server 17 generates a weight loss prediction model. As used herein, a "weight loss prediction model" is an estimate of a future weight or weight loss assuming adherence to one or both of an energy intake prescription and an energy expenditure prescription. The weight loss prediction model is determined by the cloud server 17 according to a validated differential equation as disclosed in the following publications, the contents of which are incorporated by reference in their entirety: Thomas, D. M. et al, "A simple model predicting individual weight change in humans," *J. Biol. Dyn.* 2011, 5(6):579-599; and Thomas, D. M. et al, "A computational model to determine energy intake during weight loss," *Am. J. Clin. Nutr.* 2010, 92(6):1326-1331. In addition to determining the weight loss prediction model, the cloud server 17 controls authentication, controls device integration, stores and manages content updates, and stores and manages participant data.

Figure 2:
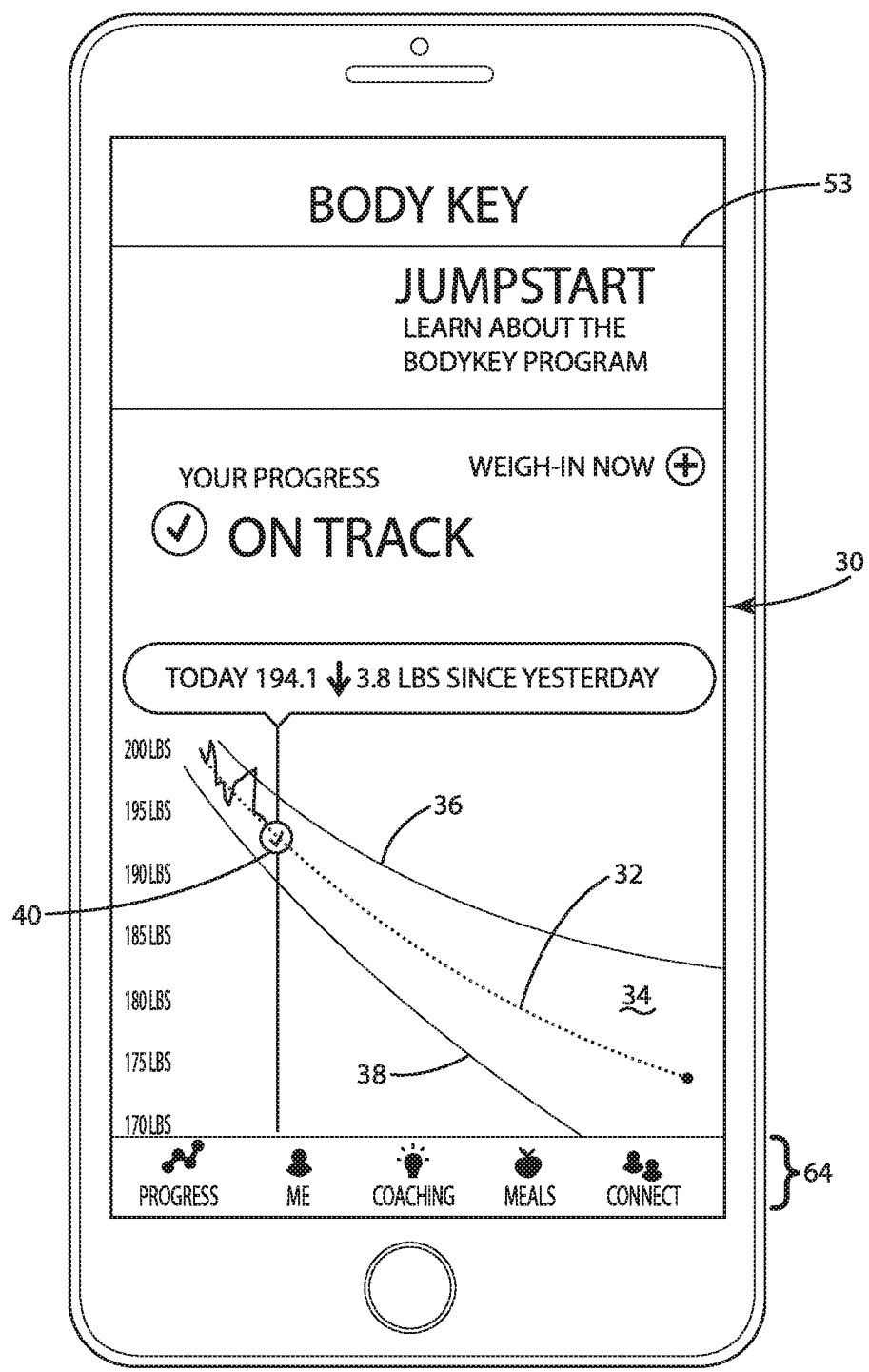
FIG. 2 illustrates a first application window of the mobile device in accordance with the embodiment of FIG. 1.

Once determined by the cloud server 17, the weight loss prediction model is communicated to the mobile device 10. In another embodiment, the weight loss prediction model is determined by the mobile device processor 16, and not the cloud server 17. In both embodiments, the weight loss prediction model is visually represented in a first application window of an application program hosted by the mobile device 10. Referring to FIG. 2, the first application window 30 is illustrated. The first application window 30 depicts the weight loss prediction model as a curved line 32. In this example, the curved line representing an expected reduction from approximately 200 lbs to 175 lbs over six months. The weight loss prediction model further includes a zone of adherence 34. The zone of adherence 34 is delimited by an upper boundary 36 and a lower boundary 38. The upper boundary 36 and the lower boundary 38 are determined by fitting an upper curve and a lower curve through the mean absolute error obtained by validation of the differential equation described in Thomas et al (2011). The participant is considered adherent if the measured body weight is within this zone.

The transition phase is the second phase in the weight loss program. The transition phase extends over a second duration, the second duration being eight weeks in the current embodiment. The transition phase focuses the participant on understanding and overcoming weight loss barriers, while also continuing with an energy intake prescription, but with a lessor reliance on meal replacement shakes—optionally one meal replacement shake per day in this phase. The transition phase includes presenting, on the mobile device, a health assessment, for example the health assessment disclosed in US Patent Application Publication 2015/0220697 to Hunt et al entitled "System and Method for Health Assessment," the disclosure of which is incorporated by reference in its entirety. The health assessment includes questions that relate to the participant's diet, physical activity, mindset, sleep, stress, and meal habits. The assessment then prioritizes barriers to the participant's adherence to a health-related recommendation. Initially, the barriers include a default prioritization: eating mindset, activity mindset, sleep, stress, and meal habits. The sequence of SmartTips and SmartLoss™ feedback during this transition phase is determined based on the prioritization of these barriers. If the participant experiences all barriers, or no barriers, the participant will receive feedback in accordance with the default prioritization. If the participant experiences only some barriers, topics identified as barriers are addressed first and topics not identified as barriers are addressed last while maintaining their default barrier ranking.

The steadfast phase is the third phase in the weight loss program. The steadfast phase extends over a third duration, the third duration being eight weeks in the current embodiment. During this phase, the participant continues to receive feedback in a cadence that is determined based, at least in part, on the results of the health assessment at the beginning of the transition phase. The steadfast phase also includes the same energy intake prescription as during the jumpstart phase and the transition phase. However, the participant is presented with increased meal options from which to choose during the steadfast phase, with a more limited reliance on meal replacement shakes, for example on an as-need basis.

The sustain phase is the fourth and final phase in the weight loss program. The sustain phase extends over a fourth duration, the fourth duration being four weeks in the current embodiment. Throughout this phase, the mobile device 10 prompts the participant with a series of questions, the results of which are used by the processor 16 to determine if the participant is interested in a further six-month weight loss program or if the participant is interested in learning about optimized nutrition, or beauty related products. The mobile device 10 then provides targeted feedback messages that introduce the participant to products of interest based on the answers received from the participant.

Over the course of the weight loss program, the reliance on meal replacement shakes reduces. During the jumpstart phase, the participant is scheduled to receive two meal replacement shakes per day. During the transition phase, the participant is scheduled to receive one meal replacement shake per day. During the sustain phase, the participant may receive no meal replacement shakes, or may receive an as-needed meal replacement shake. In its place, the participant is provided with portion guidance in accordance with the energy intake prescription. As discussed in Part VI below, for example, the participant is provided with a portion allotment by category (carbs, protein, fats). By adhering to the portion allotment for each category, the participant adheres to the energy intake prescription and is predicted to lose weight according to the weight loss prediction model.

The weight loss program additionally includes a recurring series of (approximately) bi-weekly assessments. Beginning in the steadfast phase, the bi-weekly assessments are presented on the mobile device 10 and include questions that relate to the participant's physical activity and life events that may pose challenges to sustained weight loss. The results of the bi-weekly assessments can be used to determine the content of SmartTips and SmartLoss™ feedback (discussed below) and can be used to determine any interest in repeating the weight loss program.

III. Weight Loss Tracking and Performance Flags

As noted above in connection with FIG. 2, the current embodiment includes a graphical user interface 22 hosted on a mobile device 10 that visually depicts the weight loss prediction model in the first application window. The first application window additionally depicts a plurality of weight measurements over time, the plurality of weight measurements being superimposed over the weight loss prediction model. As discussed below, the plurality of weight measurements includes weight measurements from a connected weight scale 12 and/or weight measurements that are manually entered into the mobile device 10 by the participant.

In the current embodiment, the most recent of the depicted weight measurements is illustrated as a performance flag 40. The performance flag 40 is selected from among a plurality of performance flags based on a measure of conformance with the weight loss prediction model. As shown in FIG. 3, the plurality of performance flags includes a first (green) performance flag, a second (yellow) performance flag, and a third (red) performance flag. Different colors can be used in other embodiments as desired. The first, second and third performance flags are discussed in turn.

The green performance flag 42 generally indicates conformance with the weight loss prediction model for the current day. In the current embodiment, the green performance flag is presented if the most recent of the depicted weight measurements is within the zone of adherence 34, is less than the prior day's weight measurement, and is at least a predetermined amount (e.g., one pound) below the upper boundary 36. The green performance flag is depicted in FIG. 3 and includes a solid green circle with a checkmark, which can be replaced with a solid green circle with a star for milestone achievements 48, for example a milestone weight loss, e.g., the amount of weight lost, the percent of weight lost, and whether the weight loss goal is achieved.

The yellow performance flag 44 generally indicates a number of scenarios that reflect less than general conformance with the weight loss prediction model. In the current embodiment, the yellow performance flag is presented if the most recent of the depicted weight measurements is within the zone of adherence 34 but (a) is approximately the same as the prior day's weight measurement, (b) is greater than the prior day's weight measurement, or (c) is within a predetermined amount (e.g., one pound) of the upper boundary 36. Also by example, the yellow performance flag is presented if the most recent of the depicted weight measurements is above the zone of adherence 34 but represents a decrease at a weekly rate of at least 0.5 pounds per week. The yellow performance flag is depicted in FIG. 3 and includes a solid yellow circle with an exclamation mark, but can differ in other embodiments.

The red performance flag 46 generally indicates the participant is not in conformance with the weight loss prediction model for at least the current day. In the current embodiment, the red performance flag is presented if the most recent of the depicted weight measurements is above the zone of adherence 34 and is not decreasing at a weekly rate of at least 0.5 pounds per week. The red performance flag is also presented if the participant's weight is below the lower boundary 38 by at least five pounds for ten or more days within the immediately preceding two week period. In addition, the red performance flag is presented if the participant's body-mass-index (BMI) is below a predetermined minimum BMI. The red performance flag is depicted in FIG. 3 and includes a solid red circle with an x-mark, but can differ in other embodiments As shown in FIG. 2, the first application window depicts one weight measurement per day in the current embodiment, while in other embodiments the first application window depicts greater or fewer number of weight measurements per day. With respect to the manual entry of weight data, the participant is permitted to manually enter weight data for the current calendar day and the previous calendar day, and may edit the weight data only once. With respect to weight data from a connected weight scale 12, the participant is permitted to manually edit weight data for the current calendar day and the previous day. As shown in FIG. 3, however, manually entered weight data and manually edited weight data is visually depicted in a manner that is different from unedited weight data from a connected weight scale 12. In particular, manually entered weight data and manually edited weight data is represented by a diamond-shaped performance flag, while weight data directly from the connected weight scale 12 is represented by circle-shaped performance flag. Missed weight data for a given day, for example the current day, is represented by a broken open circle in the first application window.

IV. Activity Goals and Activity Tracking

Figure 4:
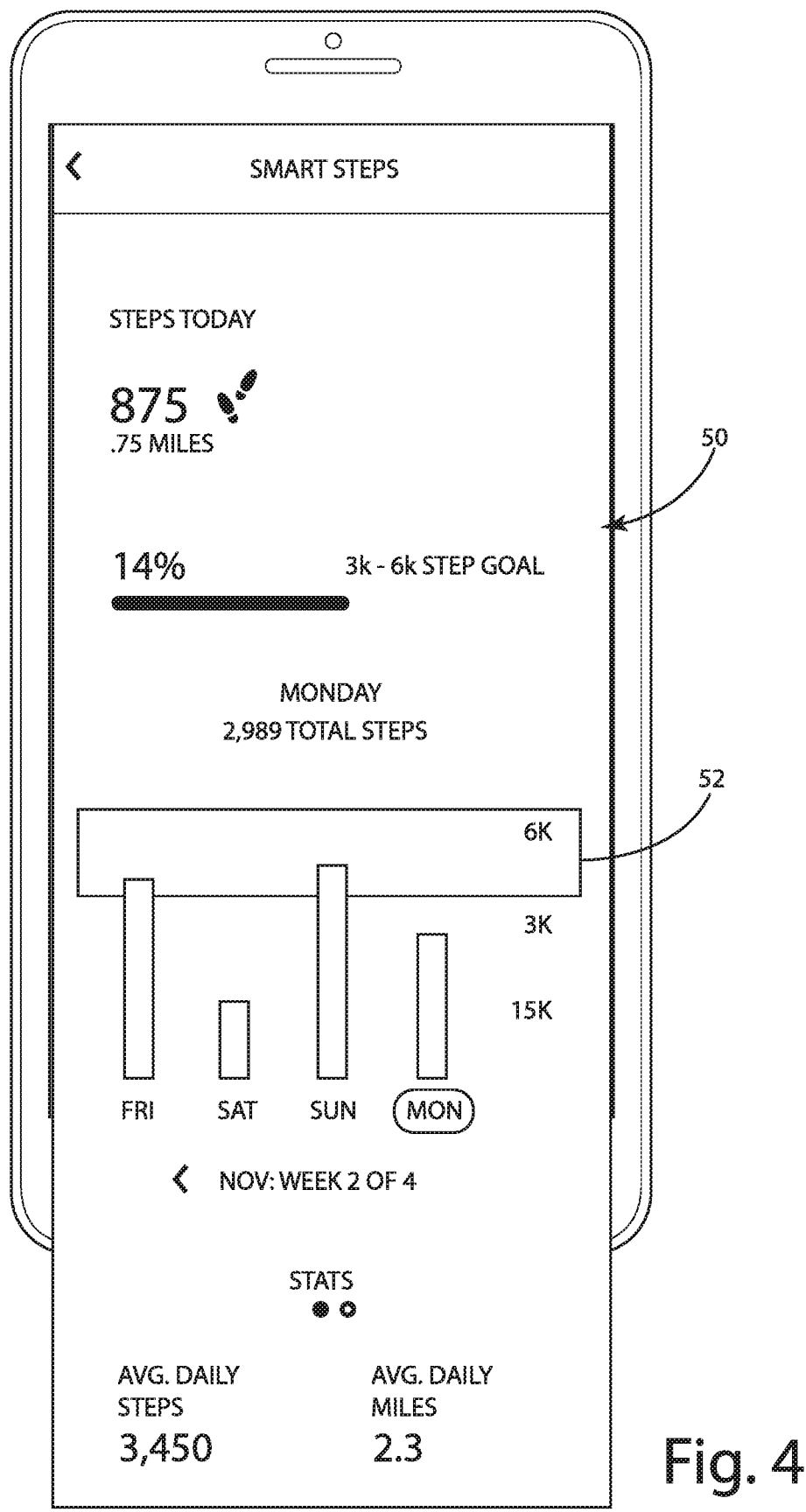
FIG. 4 illustrates a second application window of the mobile device including a step goal and historical step data.
Figure 5:
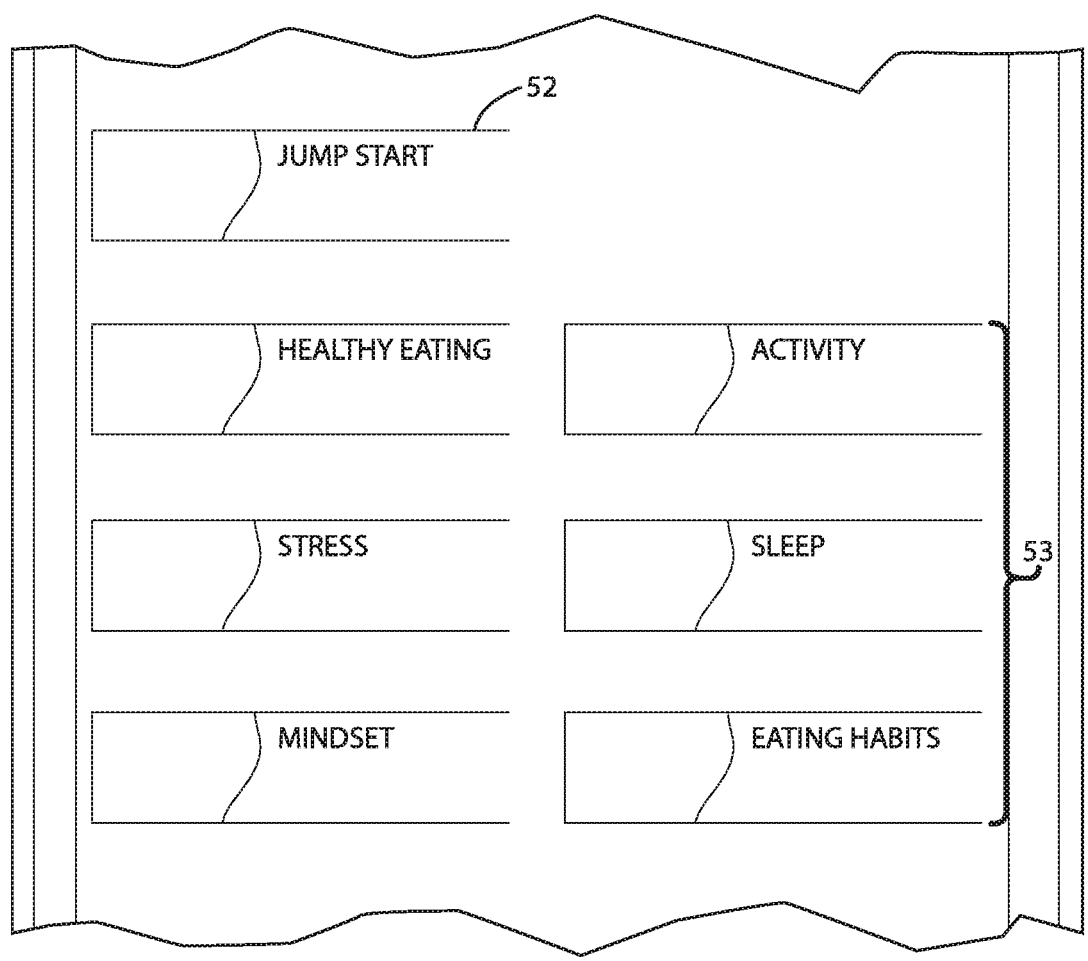
FIG. 5 illustrates selectable SmartTips feedback banners for display by the mobile device in the first application window.

In addition to providing goal setting and goal monitoring in connection with an energy intake prescription, the weight loss program provides goal setting and goal monitoring in connection with an energy expenditure prescription. As shown in FIG. 4, the graphical user interface 22 of the mobile device 10 visually depicts, in a second application window 50, an activity goal and activity tracking. The activity goal gradually increases as the participant progresses through the program. In other words, activity is introduced by establishing an initial goal for the participant and gradually increasing the goal over the course of the weight loss program. Described below as a step goal or a step goal range, the activity goal can include other activities in other embodiments.

In the current embodiment, the second application window depicts an initial step goal range, shown as a horizontal bar 52, based on the answer to at least two questions. The first question gauges the general movement of the participant throughout a typical day. For example, the participant is asked if a typical day is spent mostly sitting, sitting but standing every hour, an even mix of sitting and standing, or mostly standing. The second question gauges the general activity level of the participant throughout a typical week— e.g., the participant is categorized as "low physical activity" or "high physical activity." Based on the answers to these questions, the participant is assigned an initial step goal range for at least the first two weeks of the jumpstart phase. In the current embodiment, the step goal ranges include: 2000-4000 steps per day if the participant sits most of the day and has low physical activity; 4000-6000 steps per day if the participant sits most of the day and has high physical activity; 5000-7000 steps per day if the participant sits but is on their feet every hour and has low physical activity; 5000-7000 steps per day if the participant has an even mix of sitting and standing with low physical activity; 7000-9000 steps per day if the participant has an even mix of sitting and standing with high physical activity; 7000-9000 steps per day if the participant is mostly on their feet with low physical activity; or at least 10,000 steps per day if the participant is mostly on their feet with high physical activity. In other embodiments the initial step goal can be based on other criteria.

As noted above, the initial step goal is based on the participant's physical activity level throughout a typical week. The mobile device 10 determines the level of physical activity based on a metabolic equivalent of task (MET) calculation. The MET calculation is based on the intensity, time, and number of days the participant exercises in a given week. For light intensity exercise, the MET value is 3.3 times the number of minutes and the number of days of the exercise. For moderate intensity exercise, the MET value is 4.0 times the number of minutes and the number of days of the exercise. For vigorous intensity exercise, the MET value is 8.0 times the number of minutes and the number of days of the exercise. The threshold MET value between low physical activity and high physical activity is set at 600 MET in the present embodiment, but can vary in other embodiments.

At the conclusion of the first two weeks of the jumpstart phase, the mobile device 10 generates a new step goal, or "first revised step goal," based on the median daily step count and the performance flags for the first two weeks. For example, if the participant received only green flags for each day during the first two weeks—indicating conformance with the weight loss prediction model—the first revised step goal is 110% of the median daily step count for the first two weeks, optionally rounded up or down to the nearest 500 steps. If the participant received a yellow flag for any day during the first two weeks, the first revised step goal is 105% of the median daily step count for the first two weeks, optionally rounded up or down to the nearest 500 steps. If the participant received a red flag for being above the zone of adherence 34 for any day during the first two weeks, the first revised step goal is unchanged.

Thereafter, the mobile device 10 adjusts this step goal, on a recurring weekly basis, based on the performance flags from the previous week. If the participant received all green flags for the previous week and achieved the current step goal, the next revised step goal is 110% of the current step goal, rounded up or down to the nearest 500 steps. If the participant received a yellow flag for any day during the previous week, the mobile device 10 increases the step goal by 5%, optionally rounded up or down to the nearest 500 steps. If the participant received a red flag for being above the zone of adherence 34 for any day during the previous week, the mobile device 10 maintains the existing step goal. The foregoing step goal adjustment is repeated throughout the weight loss program, with the goal of increasing the participant's step count to a median of 10,000 steps per day. The foregoing step goal adjustment is repeated at the end of each seven day period, with a seven day lookback, throughout the weight loss program, with the goal of increasing the participant's step count to a median of 10,000 steps per day by the end of the weight loss program.

To reiterate, the current embodiment includes a graphical user interface 22 hosted on a mobile device 10 that visually depicts, in the second application window 50, the participant's median daily step count as measured by a step counter 14, or other activity as measured by a caloric energy expenditure device, and that depicts a first step goal 52 based on an activity assessment. At the conclusion of two weeks, the second application window 50 replaces the first step goal with a second step goal that is based, in one embodiment, on a measure of conformance of the participant's measured weight relative to the weight loss prediction model. On a weekly basis thereafter, the second step goal includes a first percentage increase in response to each of the performance flags from the prior week being green performance flags, a second percentage increase, less than the first percentage increase, in response to any one of the performance flags from the prior week being yellow performance flags, or no increase in response to any one of the performance flags from the prior week being red performance flags. This process repeats at least until the participant's median daily step count achieves a target median step count, for example 10,000 steps per day.

V. Pre-Programmed Feedback

As noted above, the mobile device 10 provides pre-programmed feedback as part of the weight loss program, the pre-programmed feedback being structured and scheduled to provide effective behavior modification guidance. The pre-programmed feedback includes four categories of feedback in the current embodiment: SmartTips feedback, SmartLoss™ feedback, Milestone feedback, and Ad hoc feedback. Each category of feedback is discussed in turn, followed by a discussion of the frequency of SmartTips feedback and SmartLoss™ feedback.

SmartTips feedback provides educational material related to weight loss fundamentals as well as nutrition, physical activity, and lifestyle factors that may impact weight loss success. During the jumpstart phase, SmartTips feedback appears as a selectable banner 53 in the first application window 30 (shown in FIG. 2) that, when selected, opens an additional application window dedicated to the SmartTips feedback. During this phase, the selectable banner 53 is labeled "JUMPSTART" 52. Beginning in the transition phase, the selectable banner 53 includes topics such as healthy eating, activity levels, stress levels, sleep levels, mindset, and eating habits. Some of these topics relate to the barriers identified in the barrier assessment discussed in Part II (stress, sleep, mindset, and eating habits) to aid the participant in overcoming specific barriers experienced by the participant. During the steadfast phase and the sustain phase, the selectable banner 53 is labeled "STEADFAST" and "SUSTAIN," respectively. SmartTips feedback is delivered at a scheduled cadence during the jumpstart phase. SmartTips feedback is delivered in an order and at a cadence thereafter dependent upon the results of the above-mentioned barrier assessment and (in some instances) dependent upon the results of the bi-weekly assessments.

Figure 6:
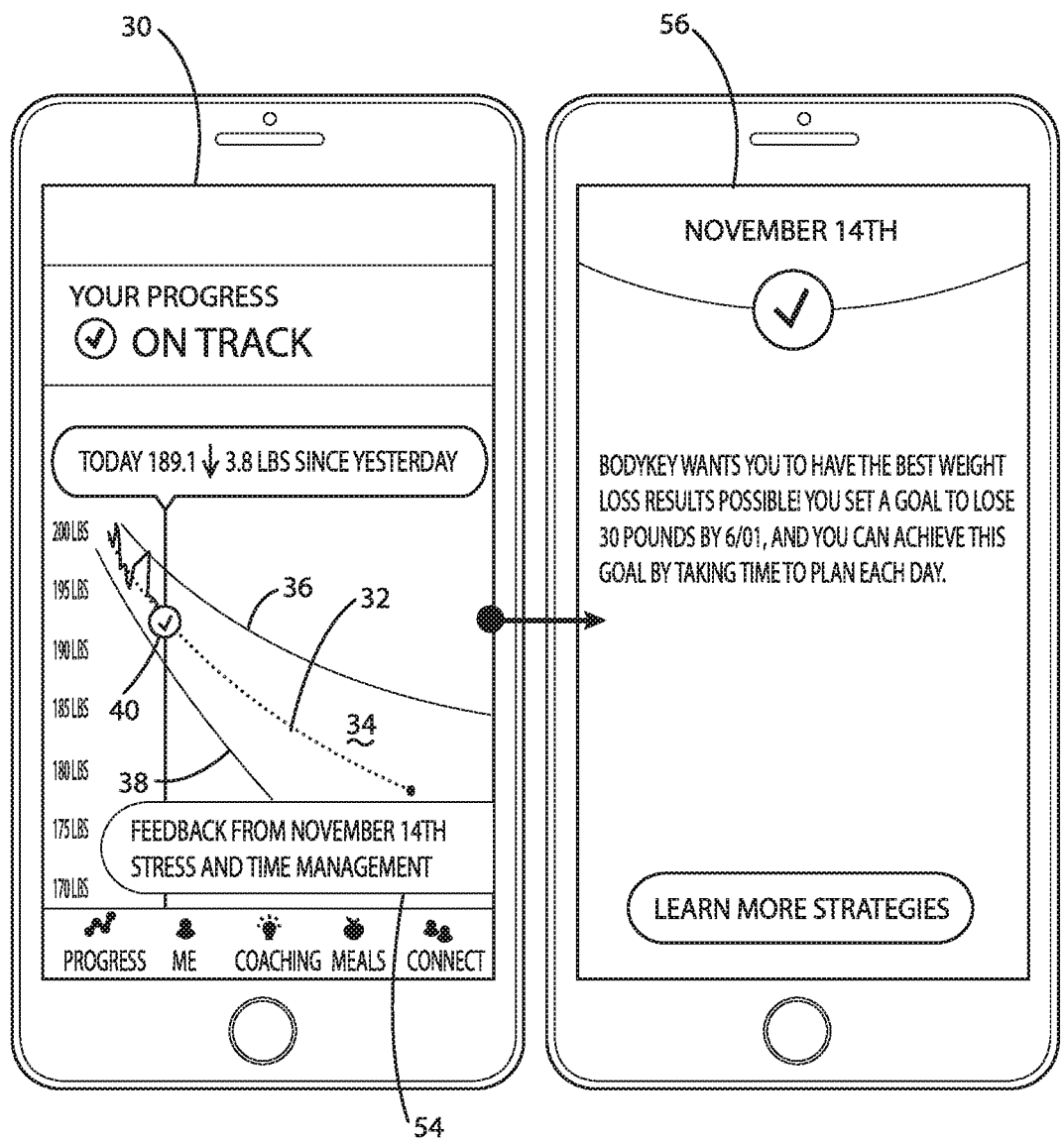
FIG. 6 illustrates the first application window of the mobile device illustrating a selectable SmartLoss™ feedback banner and an example thereof.

SmartLoss™ feedback provides informative content as a coaching message that is presented based on a measure of adherence to the weight loss prediction model. One example of SmartLoss™ feedback is illustrated in FIG. 6, in which a selectable banner 54 is depicted below the weight loss prediction model 32. When the participant selects the SmartLoss™ feedback banner 54, the mobile device 10 opens a further application window 56 with the corresponding information that is scheduled to be delivered that day. The content of the SmartLoss™ feedback depends upon the performance flag for the given day, but relates to the same overarching topic. For example, the content of the SmartLoss™ feedback is different if the most recent depicted weight measurement includes a green performance flag than for a yellow performance flag or a red performance flag. However, the content of the SmartLoss™ feedback will generally relate to the same topic regardless of the performance flag for the given day.

SmartLoss™ feedback can also contain an abbreviated health assessment, optionally in the steadfast phase and in the sustain phase. For example, the participant can be presented with statements that describe different readiness states, social challenges, and life events. Using the mobile device 10, the participant can select the statements that best describe their current state. The selections are then used by the processor 16 to determine the content for the next scheduled SmartLoss™ feedback and SmartTips feedback. Further by example, the selections are used by the processor 16 to determine the order for both SmartTips feedback and SmartLoss™ feedback over the next phase of the program. Still further by example, the abbreviated health assessment can be tailored to determine the types of products of interest to the participant. Further feedback can then be tailored to focus on these products.

Figure 7:
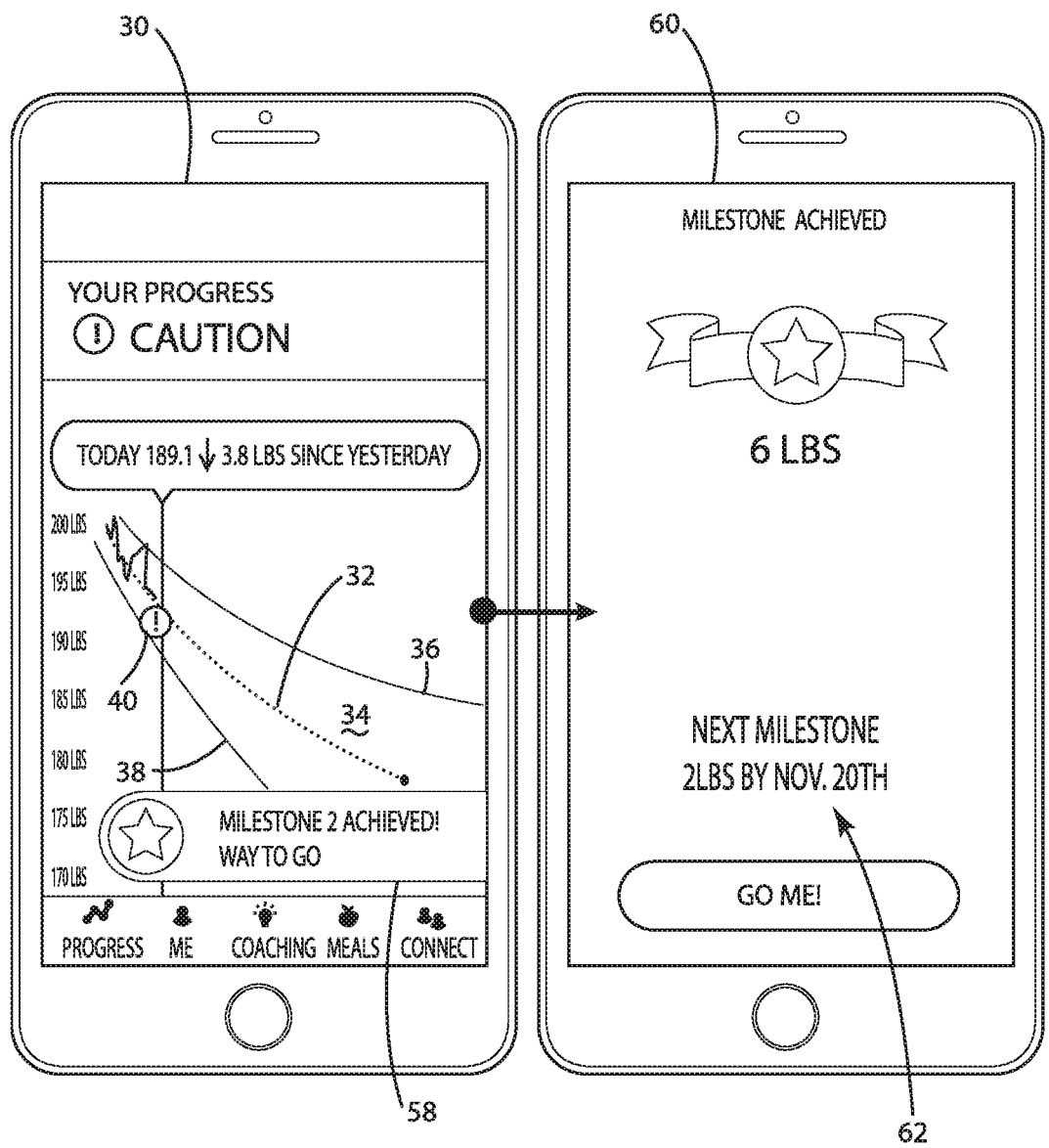
FIG. 7 illustrates the first application window of the mobile device illustrating a selectable Milestone feedback banner and an example thereof.

Milestone feedback is based on the participant reaching a predetermined weight loss milestone. The weight loss milestone can include, for example, achieving a predetermined percentage of a weight loss goal, for example 5% or 20% of a weight loss goal. Milestone feedback replaces SmartLoss™ feedback in the current embodiment, appearing as a selectable banner 58 in the first application window 30 below the weight loss prediction model 32 (shown in FIG. 7). In other embodiments, the Milestone feedback is presented in addition to the SmartLoss™ feedback. When the participant selects the Milestone feedback banner 58 in the first application window 30, the mobile device 10 opens a further application window 60 with the corresponding milestone, as well as an indication of the next scheduled milestone 62 in the weight loss program.

Ad hoc feedback is focused on topics such as weight loss during the holidays, events, promotions, and challenges. Ad hoc feedback is not generated as a function of the barrier analysis or as a function of the performance flags. Consequently, all participants in the weight loss program receive Ad hoc feedback regardless of the results of the barrier assessment or the degree of adherence to the weight loss prediction model.

The frequency of SmartTips feedback will generally depend on the phase of the weight loss program. During the jumpstart phase, the participant receives predetermined SmartTips feedback every three days. During the later phases of the weight loss program, the participant receives predetermined SmartTips feedback once per week. The content of the SmartTips feedback is determined based on the results of the initial barrier assessment and optionally based on the (approximately) bi-weekly barrier assessments, for example bi-weekly barrier assessments relating to exercise.

The frequency of SmartLoss™ feedback will also generally depend on the phase of the weight loss program. In the current embodiment, the participant receives SmartLoss™ feedback every three days during the jumpstart phase. During the later phases of the weight loss program, the participant receives SmartLoss™ feedback less frequently, dependent upon the degree of conformance with the weight loss prediction model. For example, the participant receives SmartLoss™ feedback less frequently (e.g., the $3^{rd}$ and $7^{th}$ day of the week rather than the $1^{st}$, $3^{rd}$, and $7^{th}$ day of the week) if the most recent of the depicted weight measurements includes a green performance flag. Alternatively, the processor 16 can look to historical data from a previous period to determine the cadence of feedback for the upcoming period. For example, if the participant received only green performance flags from the previous week, the SmartLoss™ feedback for the next week can be set to a lower frequency, for example on the $3^{rd}$ and $7^{th}$ day of the week. If the processor 16 determines that the participant has received yellow or red performance flags each day for a given period, the mobile device 10 can present a SmartLoss™ feedback message to motivate the participant toward the adherence with the weight loss prediction model.

To reiterate, the cadence of the foregoing feedback is variable to ensure the pre-programmed feedback does not become overly predicable. For example, the cadence of the SmartLoss™ feedback is dependent upon the performance flags. This feedback is depicted in the first application window 30 as a user-selectable banner that, when selected, provides the scheduled feedback content. Near the conclusion of the weight loss program, the SmartLoss™ feedback can include guidance regarding optimized nutrition, optimized sports nutrition, or health and beauty related products, along with the option to repeat the weight loss program.

Figure 8:
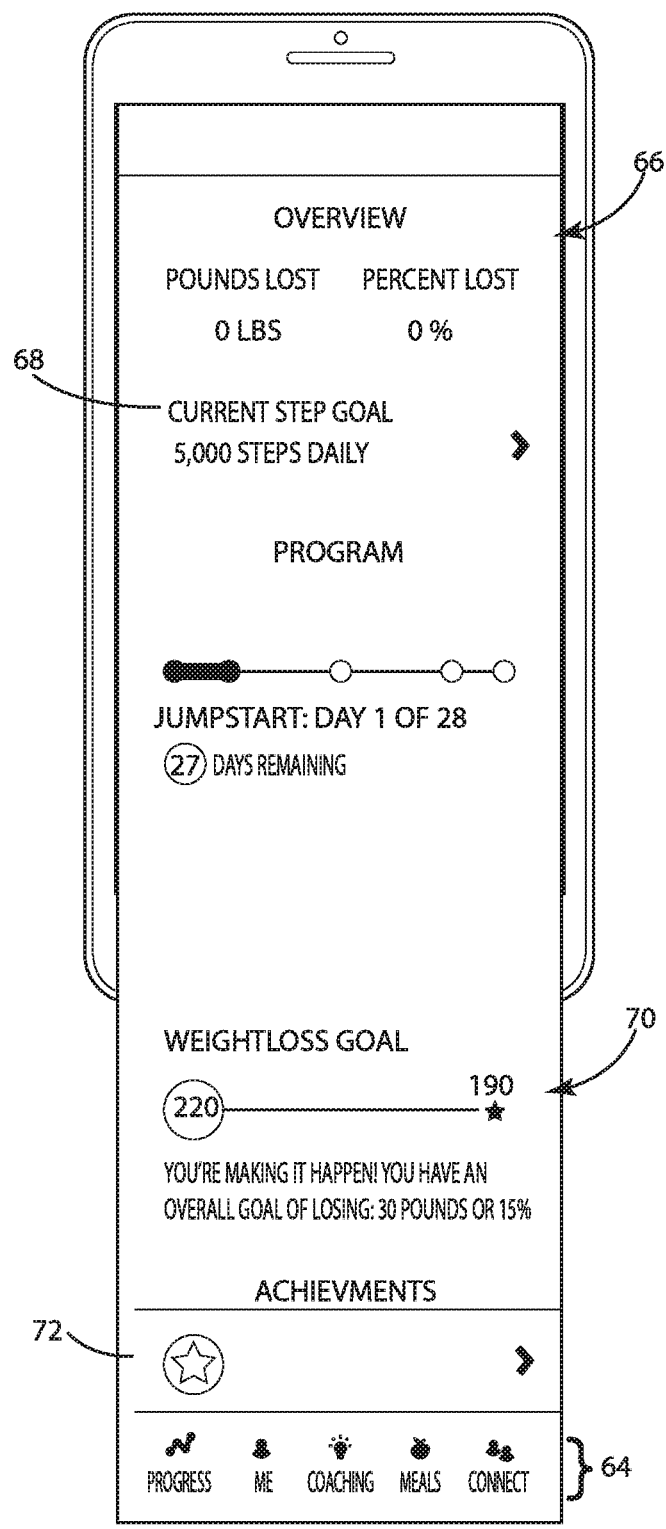
FIG. 8 illustrates the third application window of the mobile device including personalized weight loss data and goal setting.
Figure 9:
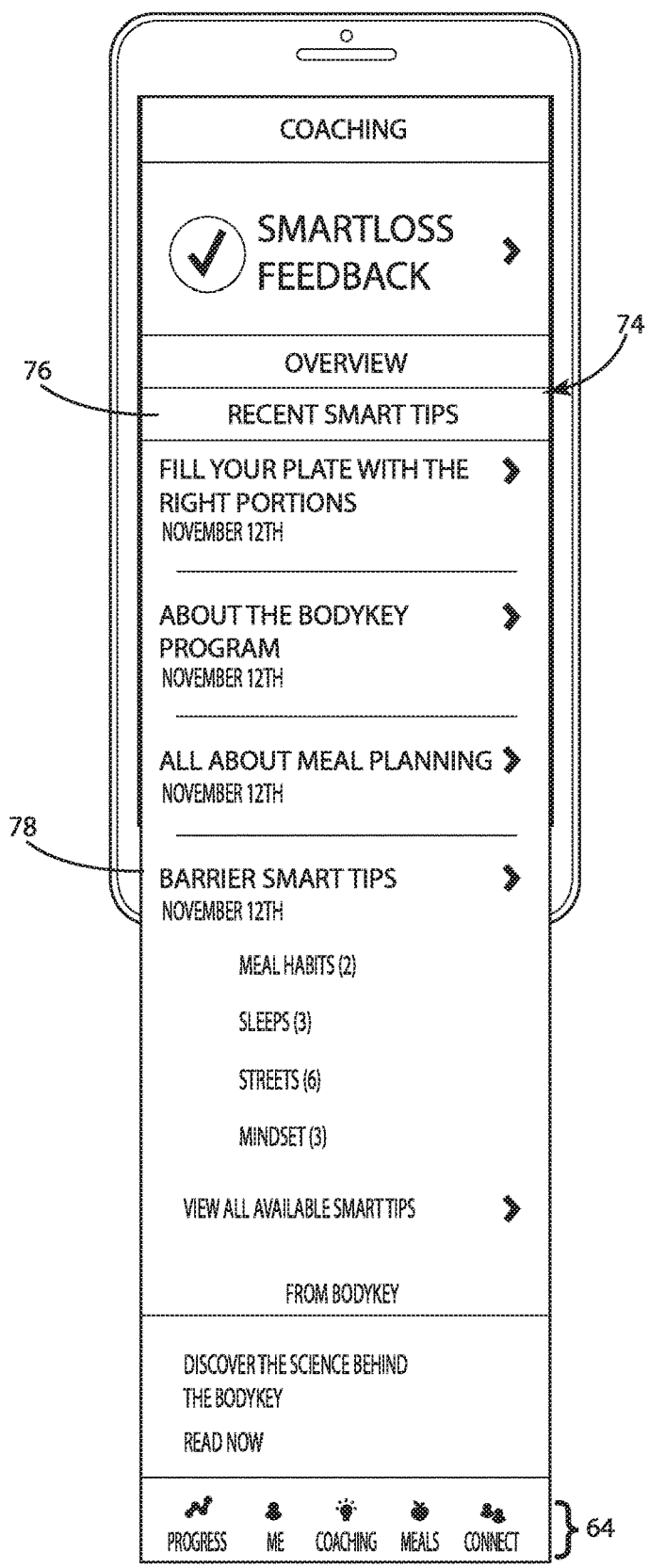
FIG. 9 illustrates the fourth application window of the mobile device including personalized coaching and archived SmartTips feedback.

Lastly, FIGS. 8 and 9 disclose further application windows 66, 74 presented on the mobile device 10, each being selectable from a menu 64 on the first application window 30. FIG. 8 depicts an application window 66 having historical data for the participant. The historical data includes the weight lost to date, both in pounds and as a percentage of the participant's starting weight. The historical data also includes the current step goal 68, the current phase of the weight loss program, the selected weight loss goal 70, and any badges or achievements 72. FIG. 9 depicts an application window 74 having coaching data. The coaching data includes recent SmartTips 76, barrier SmartTips 78, and general information about portion sizes and meal planning. The participant can return to the first application window 30 from a menu 64, which is identical to the menu 64 on the first application window 30.

VI. Portion Tracking

Figure 10:
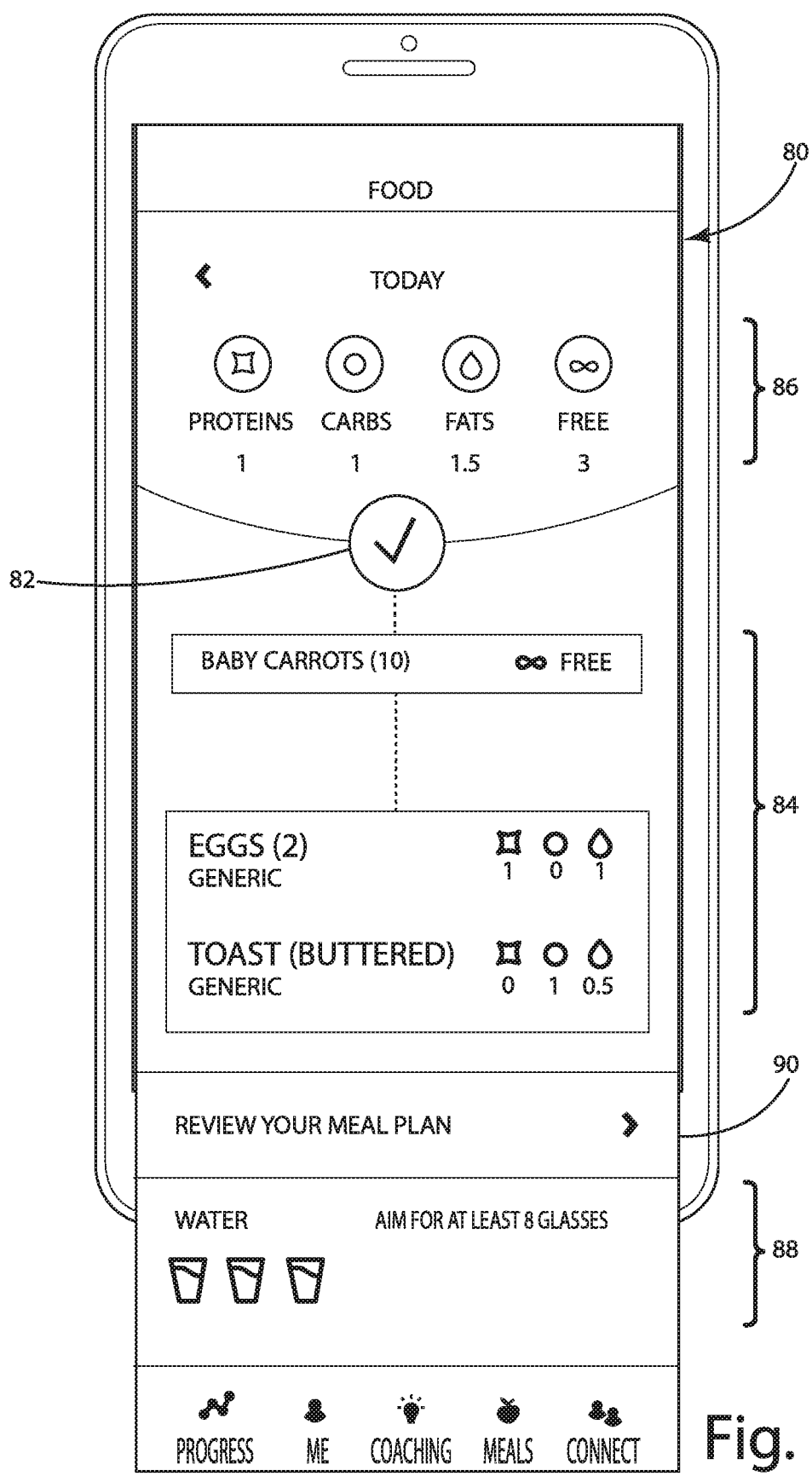
FIG. 10 illustrates the fifth application window of the mobile device including portion tracking in accordance with a meal plan.

Referring now to FIG. 10, the weight loss program provides a further application window 80 for providing portion tracking in accordance with the above-mentioned energy intake prescription. As noted above, the energy intake prescription is determined as a function of the participant's weight at the start of the weight loss program, the participant's target weight/target weight loss, and certain biometric data (e.g., gender, age, and height). The energy intake prescription includes a daily recommended caloric intake that is broken down into proteins, carbohydrates, and fats. While the daily recommended caloric intake remains constant throughout the weight loss program, the participant can select among a balanced plan, a reduced carbohydrate plan, and a reduced fat plan according to his or her preferences.

More specifically, the participant can track food intake by selecting a touch icon 82 in the application window 80 depicted in FIG. 10. The touch icon 82 opens a further window (not shown) for manual food entry, e.g., eggs, toast, and carrots in the illustrated embodiment. The processor 16 then determines the corresponding number of portions of protein, carbohydrate, or fats, which are published in a sub-window 84. The total number of portions for the current day are shown in the upper portion 86 of the application window 80 depicted in FIG. 10. Foods lacking meaningful amounts of calories are scored as "free" foods, which do not count against the daily energy intake prescription. If the total number of portions for the current day are exceeded, the application window 80 generates a warning message for the participant. The current day's water intake is also shown in the application window 80, which can be manually updated by touching the appropriate sub-window 88. The foregoing food and beverage data is saved to local memory 24 in the current embodiment, but can be saved to the server 17 in other embodiments.

Figure 11:
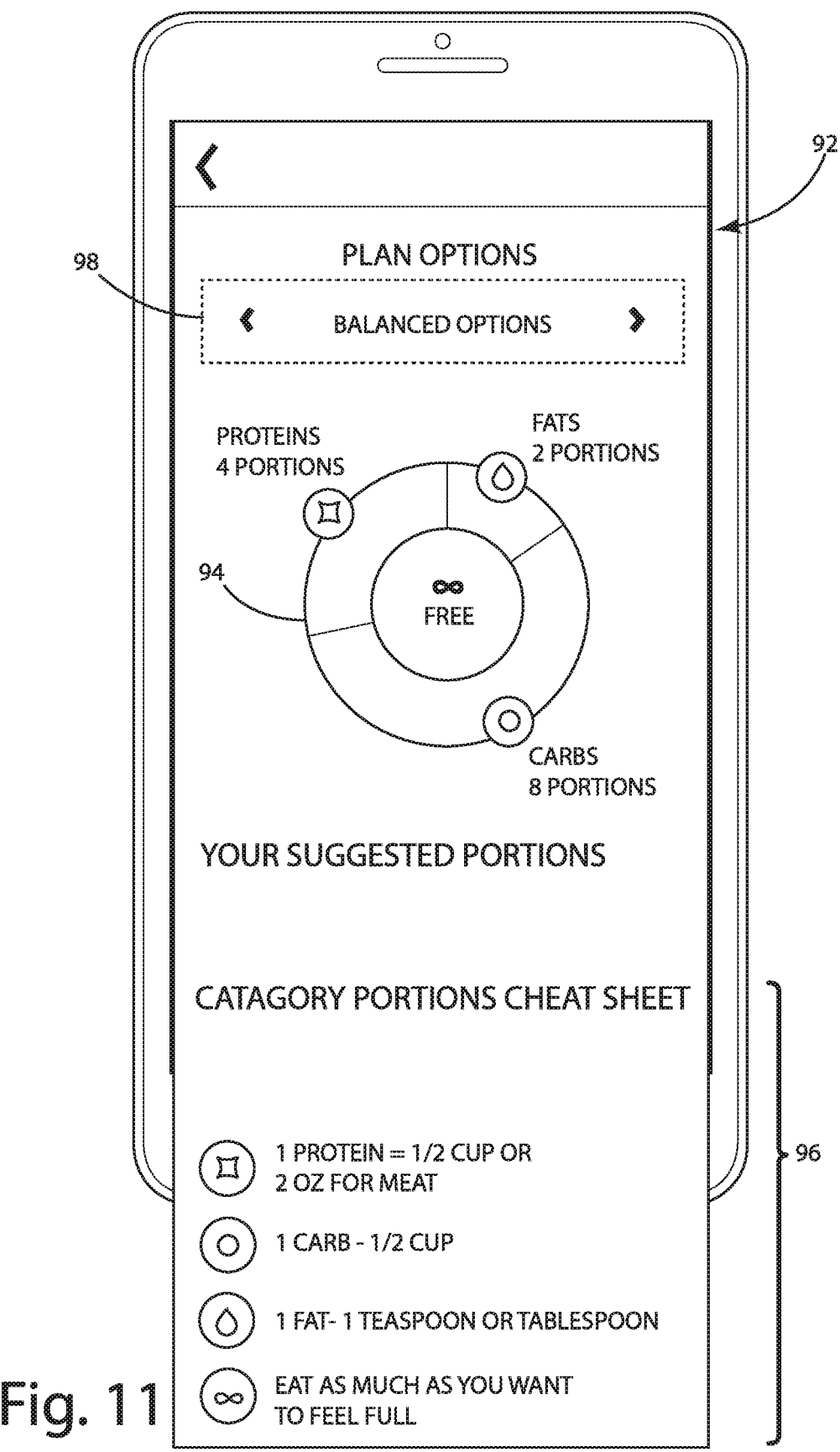
FIG. 11 illustrates the sixth application window of the mobile device including a meal plan with a daily recommended portions for proteins, fats, and carbohydrates.
Figure 12:
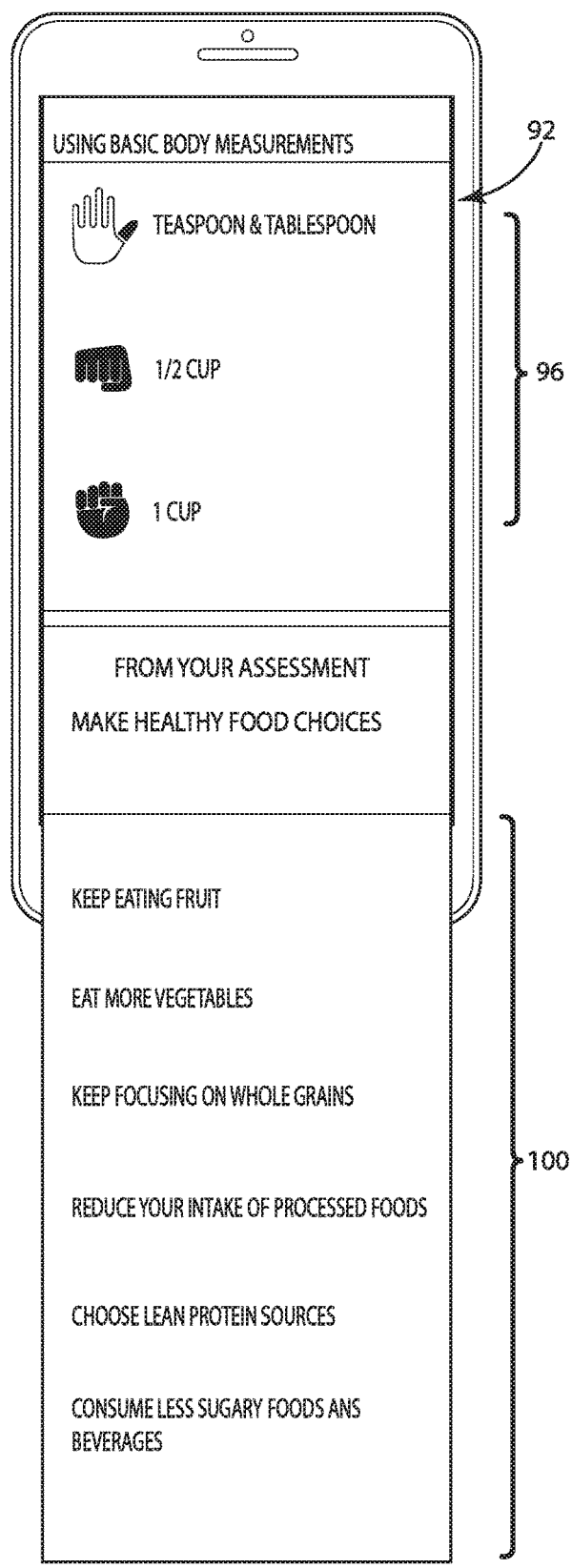
FIG. 12 further illustrates the sixth application window of the mobile device illustrating personalized coaching for the selected meal plan.

In response to a selection of the menu arrow 90 in the application window 80 shown in FIG. 10, the mobile device displays the application window 92 shown in FIGS. 11-12, which are separated onto two drawing sheets for clarity. The application window 92 in FIG. 11 identifies the current meal plan (in this example, "Balanced Option") and displays a pie-chart 94 showing the breakdown of portions that are allotted for a given day under the current meal plan. In this example, the participant is allotted four portions of protein, eight portions of carbohydrates, and two portions of fats, and unlimited portions of free foods. The application window shown in FIG. 11 also includes serving size guidance 96 for each food group. As noted above, the selected meal plan can be a balanced plan, a reduced carbohydrate plan, or a reduced fat plan. The participant can switch between these plans at any point in the weight loss program by selecting the arrows 98 in FIG. 11. Referring to FIG. 12, which as noted above is an extension of the application window 92 of FIG. 11, the application window also provides written guidance 100 to assist the participant in making healthy food choices, the written guidance being at least partially based on a prior assessment.

The graphical user interface 22 also displays recipes suggested by the processor 16 or by the server 17, the recipes being based on the participant's biometric data and/or weight loss progress. The recipes are divided into four categories: breakfast, lunch, dinner, and snacks. The recipes take into account the participant's dietary preferences, including preferences for a low fat diet, a low carbohydrate diet, or a vegetarian diet, as well as the participant's cultural background. The participant can save preferred recipes to memory 24 for quick retrieval. The graphical user interface 22 also displays the nutritional score of each recipe, including a breakdown by carbohydrates, fats, and proteins, and presents an image or photo of the recipe for the participant.

VII. Social Media Sharing

Figure 13:
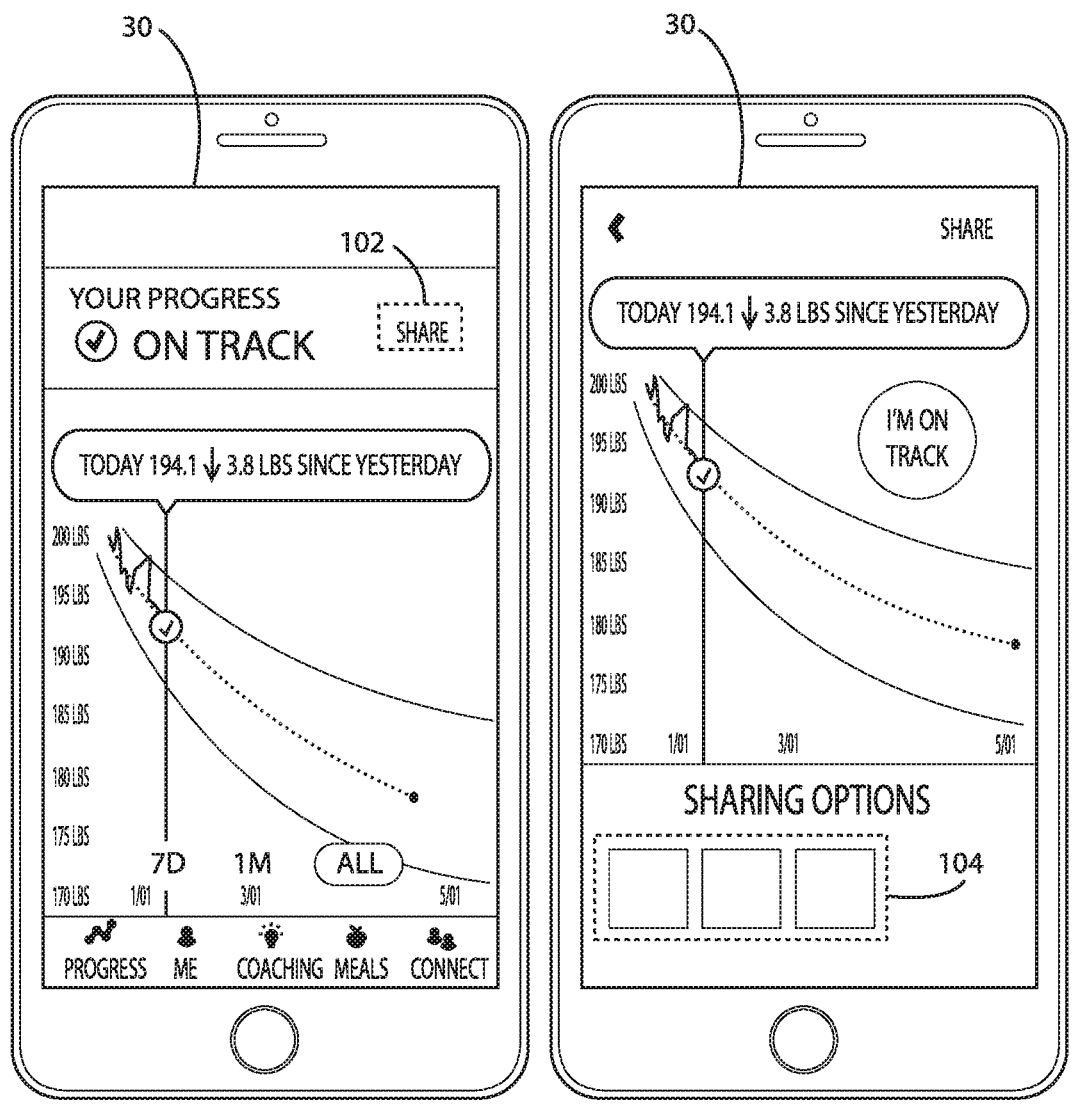
FIG. 13 illustrates an embodiment of the first application window of the mobile device with the option to share weight loss progress in social media.
Figure 14:
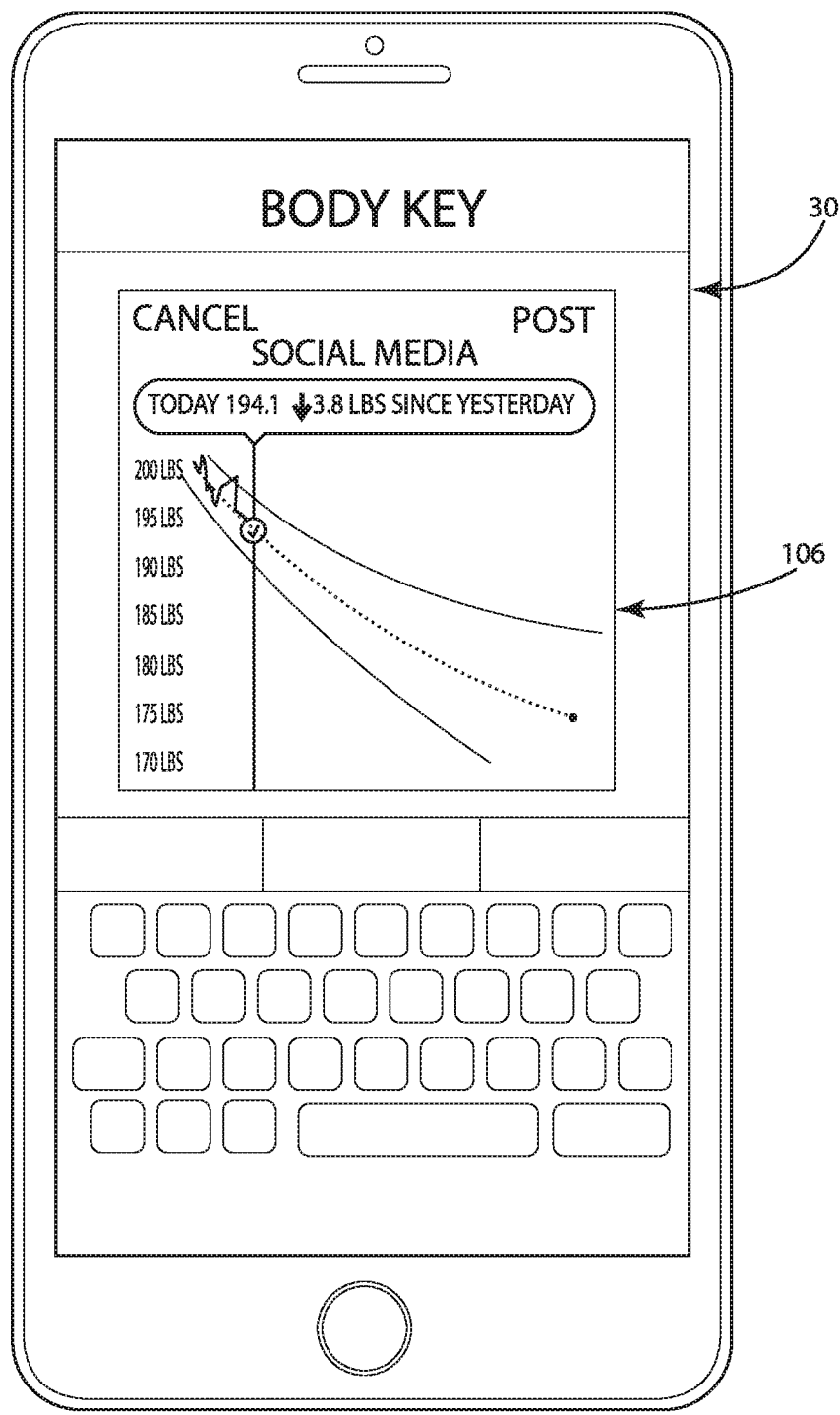
FIG. 14 illustrates the embodiment of FIG. 13 in which weight loss progress is shared in social media.

Referring now to FIGS. 13-14, the weight loss program provides the participant with multiple opportunities to publish weight loss results to social media. In particular, the first application window 30 shown in FIG. 13 includes a sharing icon 102 which, if selected, causes the first application window 30 to generate multiple sharing options 104, each with a different degree of content. That is, each sharing option 104 includes multiple weight loss reports for publishing to social media. The weight loss reports include the entire weight loss prediction model, a sub-portion of the weight loss prediction model, or only that day's performance flag. Once selected, the mobile device publishes the weight loss report to social media via the pop-up window 106 shown in FIG. 14 with the opportunity to comment and tag others if desired.

The graphical user interface 22 also includes challenges for two or more participants of the weight loss program. Challenges allow a participant to see another participant's weight loss progress (or other data) on a mobile device 10 and allow each participant to send messages to each other in the form of videos, pictures, and text. Participants can set the length of time of each challenge. Success within a challenge results in the participant receiving an award, for example a digital badge. Challenges can be one-on-one challenges or team challenges. In the case of a team challenge, a team leader has access to team member data, collective team data, and individual rankings based on weight loss progress. The leader is further provided with the ability to send messages to the team in the form of videos, pictures, and text.

Accordingly, the current embodiment provides an integrated system for delivering weight loss guidance and activity tracking in a mobile format. In this embodiment, the integrated system includes a weight loss program hosted on a mobile device. The weight loss program includes an energy intake prescription and an energy expenditure prescription and includes performance flags and various feedback that is visually depicted on the mobile device. The mobile device can be paired with a connected weight scale and a connected step counter to provide real time weight tracking and step counting. The weight loss program extends over multiple phases that are structured to help the participant gradually achieve a sustainable weight loss while increasing daily activity levels over the duration of the program. Other embodiments will differ from the current embodiment, however, which is not intended to be limiting.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A system for providing weight loss guidance to a user, the system comprising:
   a weight sensor;
   a mobile device including a graphical user interface; and
   a processor operatively coupled to at least one of the mobile device and the weight sensor, the processor including instructions that, when executed, perform the following steps:
      access a weight loss prediction model for the user based in part on a user-selected target weight loss, and
      cause the mobile device to present, in a first application window of the graphical user interface, a graphical depiction of the weight loss prediction model and at least one of a plurality of weight measurements as measured by the weight sensor over time,
      wherein the graphical depiction includes a zone of adherence having an upper boundary and a lower boundary and includes a performance flag at the most recent weight measurement in the first application window, such that the zone of adherence and the performance flag are simultaneously visible in the same first application window, the performance flag being superimposed onto the zone of adherence, and wherein the performance flag is selected from among a plurality of performance flags comprising graphical icons that are visually distinct from each other, the selection of the performance flag being based on a measure of conformance with the weight loss prediction model.

2. The system of claim 1 wherein the plurality of performance flags including a first flag indicating the most recent weight measurement is within with the zone of adherence.

3. The system of claim 2 wherein the plurality of performance flags includes a second flag indicating the most recent weight measurement is within the zone of adherence but is within a predetermined distance from an upper boundary of the zone of adherence.

4. The system of claim 2 wherein the plurality of performance flags includes a second flag indicating the most recent weight measurement is within the zone of adherence but is greater than or equal to the immediately preceding depicted weight measurement.

5. The system of claim 2 wherein the plurality of performance flags includes a third flag indicating the most recent weight measurement is above the zone of adherence but represents a measured rate of weight loss that is greater than a threshold rate of weight loss.

6. The system of claim 2 wherein the plurality of performance flags includes a third flag indicating the most recent weight measurement is not within with the zone of adherence.

7. The system of claim 1 wherein the processor is further operable to cause the graphical user interface to depict a feedback message that is selected by the processor from among a plurality of feedback messages based on the performance flag for the most recent depicted weight measurement.

8. The system of claim 1 wherein the weight loss prediction model is determined by a remote server that is connected to the mobile device over a network.

9. The system of claim 1 wherein the mobile device is a smartphone and wherein the weight sensor is an electronic weight scale in electrical communication with the mobile device.

10. The system of claim 1 wherein the processor is further adapted to present a recommended step count in a second application window.

11. The system of claim 1 wherein the mobile device is further operable to receive a food log entry from the user in a third application window.

12. The system of claim 11 wherein the processor is further operable to convert the food log entry into a protein portion value, a carbohydrate portion value, and a fat portion value.

13. The system of claim 12 wherein the processor is further operable to cause the mobile device to present, in the third application window, the protein portion value, the carbohydrate portion value, and the fat portion value.

14. The system of claim 1 wherein the processor is further operable to cause a weight loss report to be published to social media.

15. The system of claim 14 wherein the weight loss report is selectable at the mobile device from among a plurality of weight loss reports.

16. A system for providing weight loss guidance to a user, the system comprising:
a weight sensor;
a caloric expenditure measuring device;
a mobile device including a graphical user interface; and
a processor operatively coupled to at least one of the weight sensor, the caloric expenditure measuring device, and the mobile device, the processor including instructions that, when executed, perform the following steps:
determine a weight loss prediction model for the user based in part on a user-selected target weight loss,
determine an initial activity goal for the user based on a first activity assessment presented to the user,
cause the graphical user interface to depict, in a first application window, the weight loss prediction model and a first plurality of weight measurements from the weight sensor, wherein the weight loss prediction model is depicted as a zone of adherence having an upper boundary and a lower boundary, and wherein a most recent one of the first plurality of weight measurements includes a performance flag as a graphical icon selected from among a plurality of visually distinct graphical icons based on a measure of adherence to the weight loss prediction model, the performance flag being superimposed onto the zone of adherence, such that the performance flag and the zone of adherence are simultaneously visible on the first application window,
cause the graphical user interface to depict, in a second application window, the initial activity goal and an achieved activity from the caloric expenditure measuring device,
determine a first revised activity goal based in part on the performance flag for each of the first plurality of weight measurements, and
cause the graphical user interface to depict, in the second application window, the first revised activity goal.

17. The system according to claim 16 wherein the initial activity goal is an initial step goal, the achieved activity is a median step count, and the first revised activity goal is a first revised step goal.

18. The system according to claim 17 wherein the first revised step goal represents a first percentage increase of the initial step goal in response to each of the first plurality of weight measurements being in conformance with the weight loss prediction model.

19. The system according to claim 18 wherein the first revised step goal represents a second percentage increase of the initial step goal, being less than the first percentage increase of the initial step goal, in response to at least one of the first plurality of weight measurements not being in conformance with the weight loss prediction model.

20. The system according to claim 17 wherein the processor is further configured to determine a second revised step goal based on a second plurality of weight measurements relative to the weight loss prediction model.

21. The system according to claim 17 wherein the processor is further configured to determine a second revised step goal based on whether the user achieved the initial step goal and based on a second plurality of weight measurements relative to the weight loss prediction model.

22. The system according to claim 20 wherein the second revised step goal is one of:
a first percentage increase of the first revised step goal in response to each of the second plurality of weight measurements being in conformance with the weight loss prediction model,
a second percentage increase of the first revised step goal, less than the first percentage increase of the first revised step goal, in response to fewer than all of the second plurality of weight measurements being in conformance with the weight loss prediction model, and
a zero percentage increase of the first revised step goal in response to at least one of the second plurality of weight measurements not being in conformance with the weight loss prediction model.

23. The system of claim 16 wherein the performance flag is selected from among a plurality of performance flags, the plurality of performance flags including a first flag indicating a weight measurement is within the zone of adherence and including a second flag indicating a weight measurement is not within the zone of adherence.

24. The system of claim 23 wherein the plurality of performance flags includes a third flag indicating a weight measurement is within the zone of adherence and is within a predetermined distance from an upper boundary of the zone of adherence.

25. The system of claim 23 wherein the plurality of performance flags includes a third flag indicating a weight measurement is within the zone of adherence and is greater than or equal to a previous weight measurement.

26. A system for delivering weight loss guidance to a user, the system comprising:
a mobile device including a graphical user interface and a processor, the processor including instructions that, when executed, cause the mobile device to perform the following steps:
access a weight loss prediction model based on user biometric data and a user-selected target weight,
cause the graphical user interface to present, in a first application window, a graphical depiction of the weight loss prediction model and a first plurality of daily weight measurements over a first phase, wherein the graphical depiction of the weight loss prediction model is depicted as a zone of adherence having an upper boundary and a lower boundary, and wherein a most recent one of the first plurality of daily weight measurements is depicted as a first performance flag comprising a graphical icon selected from among a plurality of visually distinct graphical icons, the first performance flag being superimposed onto the zone of adherence, such that the first performance flag and the zone of adherence are simultaneously visible on the first application window,
at the conclusion of the first phase, cause the graphical user interface to provide a plurality of questions to assess the impact of predetermined weight loss barriers on the user,
based on answers to the plurality of questions received at the graphical user interface, ranking the predetermined weight loss barriers for the user, cause the graphical user interface to present, in the first application window, a graphical depiction of the weight loss prediction model and a second plurality of daily weight measurements over a second phase, wherein a most recent one of the second plurality of daily weight measurements is depicted as a second performance flag comprising a graphical icon selected from among the plurality of visually distinct graphical icons, within the second phase, cause the graphical user interface to provide, in a second application window that is accessible through the first application window, periodic strategies for overcoming the predetermined weight loss barriers, the periodic strategies being scheduled based on the ranking of the predetermined weight loss barriers by the processor.

27. The system of claim 26 wherein the biometric data includes age, gender, height and weight.

28. The system of claim 26 wherein the predetermined weight loss barriers include eating mindset, activity mindset, sleep, stress, and meal habits.

29. The system of claim 26 wherein the processor is incorporated into the mobile device, the mobile device being one of a wearable device and a handheld device.

30. The system of claim 26 wherein the processor is hosted on a cloud server that is remotely located with respect to the mobile device.

31. The system of claim 26 wherein the first performance flag is selected from among a plurality of performance flags based on a measure of conformance with the weight loss prediction model.

32. The system of claim 26 wherein the processor is further operable to cause the graphical user interface to present a dietary regimen to the user.

33. The system of claim 32 wherein the dietary regimen includes a caloric restriction over a prescribed time period.

34. The system of claim 32 wherein the dietary regimen includes a plurality of meal replacements and portion limits.

* * * * *